United States Patent
Su et al.

[11] Patent Number: 5,728,727
[45] Date of Patent: Mar. 17, 1998

[54] ANTIOSTEOPOROTIC COMPOUND

[75] Inventors: Michael H. Su, Bellevue; Margaret I. Hosken, Bothell; Brian J. Hotovec, Woodinville; Terra L. Johnston, Seattle, all of Wash.

[73] Assignee: American Home Products Corporation, Madison, N.J.

[21] Appl. No.: 725,367

[22] Filed: Oct. 3, 1996

[51] Int. Cl.$^6$ .................... A61K 31/35; C07D 313/00
[52] U.S. Cl. .................................. 514/450; 549/354
[58] Field of Search .................... 549/354; 514/450

[56] References Cited

FOREIGN PATENT DOCUMENTS

| 08231551 | 9/1996 | Japan . |
| 08231552 | 9/1996 | Japan . |

*Primary Examiner*—C. Warren Ivy
*Assistant Examiner*—Evelyn Huang
*Attorney, Agent, or Firm*—Arnold S. Milowsky

[57] ABSTRACT

A compound of Formula I, which is named {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one, and which is useful in inhibiting bone resorption, and treating and inhibiting osteoporosis.

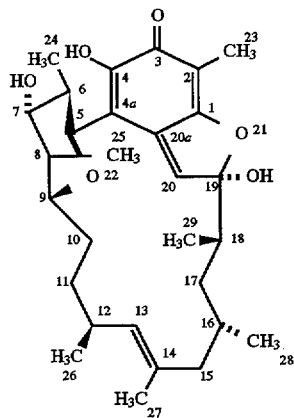

2 Claims, No Drawings

ANTIOSTEOPOROTIC COMPOUND

BACKGROUND OF THE INVENTION

Osteoporosis is a skeletal disorder which is evidenced by an increase in fracture incidence resulting from a decrease in bone density. In fact, both the bone mineral (calcium phosphate called "hydroxyapatite") and the bone matrix (major protein called "collagen") are lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the spine. At older ages, the brittleness of the bones becomes evident by the ease with which the proximal femur ("hip") fractures. Osteoporosis is the most common cause of fractures in people over age 45.

Although the cause of osteoporosis is poorly understood, it is believed that there is an imbalance between bone production and bone resorption (bone break-down). Bone remains a dynamic tissue throughout the life of an animal. That is, new bone is continuously being formed and old bone is continuously being resorbed. However, in animals suffering from an osteoporotic condition, net bone resorption exceeds bone formation.

A survey indicates that in the United States there may be fifteen to twenty million people afflicted with osteoporosis [W. A. Peck (Chairman), NIH Osteoporosis Consensus Conference, J. Am. Med. Assoc., 10, 252:799–802 (1984)]. Various types of osteoporosis are designated according to special conditions believed to be causative: senile (aging); post-menopausal (female loss of estrogenesis); disuse (chronic immobilization); steroid (long term steroid treatment as in arthritis); hypercalcemia of malignancy. Osteoporosis may also be manifested in dental problems since the mandible appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorous, Vitamin D, calcium salts, fluorides and calcitonin.

Estrogen replacement therapy has been the therapy of choice for osteoporosis in post-menopausal women.

Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, over strenuous exercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass in adults. Calcitonin, a 32 amino acid polypeptide hormone, regulates plasma calcium by decreasing intestinal calcium absorption, increasing urinary calcium excretion, and inhibiting osteoclast-mediated osteolysis (hypocalcemic effects). The bone resorption inhibitory activity of calcitonin has proven therapeutically useful in the treatment of high turnover metabolic bone diseases such as Paget's Disease, hypercalcemia of malignancy, and post-menopausal osteoporosis. Although the safety and efficacy of calcitonin has been well demonstrated, delivery of the orally-inactive peptide, either by parental administration or nasal spray, has limited the prophylactic use in asymptomatic individuals.

DESCRIPTION OF THE INVENTION

This invention provides a compound of Formula I, which is named {5R*-[6R*, 7S*, 8R*, 9R*, 12S*, 16S*, 18S*, 19S*, (13E)]} 4, 7, 9-trihydroxy-2, 6, 8, 12, 12, 14, 16, 18-heptamethyl-6, 7, 8, 9, 10, 11, 12, 15, 16, 17, 18-hendecahydro-1, 19:5, 9-diepoxybenzocyclooctadecen-3 (5H)-one, and which is useful in inhibiting bone resorption, and treating and inhibiting osteoporosis. The structure of the compound of Formula I is shown below.

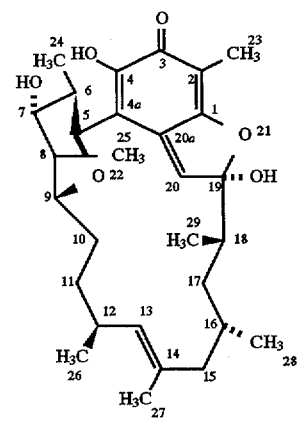

As used in describing this invention, 5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one and the compound of Formula I are used interchangeably.

{5R*-[6R*, 7S*, 8R*, 9R*, 12S*, 16S*, 18S*, 19S*, (13E)]} 4, 7, 19-Trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one is produced by culturing an actinomycete of the genus Streptomyces spp., that was designated NRRL 21370, in an aqueous nutrient medium. NRRL 21370 has been deposited under the Budapest Treaty with the Northern Utilization and Research Division, Agricultural Research Service, U.S. Department of Agriculture, Peoria, Ill, U.S.A.

This invention also provides a compound of Formula I substantially free of actinomycete protein, which is useful in inhibiting bone resorption, and treating or inhibiting osteoporosis.

This invention also relates to substantially pure compound of Formula I, which is useful in inhibiting bone resorption, and treating or inhibiting osteoporosis. Substantially pure is defined as being in excess of 75% purity.

This invention additionally provides a pharmaceutical composition comprising a compound of Formula I and a pharmaceutical carrier.

The stereochemistry designated for the compound of Formula I represents the relative stereochemical assignments at the optically active centers. This invention covers both absolute configurations of the compound of Formula I.

{5R*-[6R*, 7S*, 8R*, 9R*, 12S*, 16S*, 18S*, 19S*, (13E)]} 4, 7, 19-Trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one can be obtained by aerobic fermentation of NRRL 21370 using standard fermentation, isolation, and purification techniques, as described in Example 1. The isolation and purification of {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one is provided in Example 2.

The ability of {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one to inhibit bone resorption and treat or inhibit osteoporosis was established in three in vitro and one in vivo standard pharmacological test procedures.

The first in vitro standard pharmacological test procedure measures the ability of the compound to be evaluated to bind to the calcitonin receptor. The following describes the procedure used and the results obtained.

Adult female or male Sprague-Dawley rats (250–350 gm), were euthanized by $CO_2$ asphyxiation. Kidneys were removed and placed in ice cold saline; all subsequent procedures were carded out at 4° C. Kidneys were decapsulated and coarsely minced with scissors. The resulting fragments were homogenized in homogenization buffer (10% w/v: 250 mM sucrose; 20 mM Tris-HCl, pH 7.5; 1 mM EDTA; and 0.5 mM Phenylmethylsulfonyl fluoride (PMSF) by Polytron homogenization with two 15 seconds bursts in a cold room. The homogenate was centrifuged (4° C.) at 1000×g for 10 min. The pellet was discarded and the supernatant was centrifuged (4° C.) at 3000×g for 10 min. The pellet was discarded and the supernatant was centrifuged (4° C.) at 22000×g for 15 min. The pellet was washed 1× with 7 ml of membrane buffer (40 mM Tris-HCl, pH 7.5; 10 mM $MgCl_2$; 1 mM EGTA; 0.2 mM PMSF) per 2 kidneys by resuspension with 5 strokes of a Dounce homogenizer (tight pestle), recentrifuged at 22000×g for 15 min., and resuspended in 5 ml of membrane buffer per 2 kidneys by Dounce homogenization.

Wallac Printed Filtermat B (for use with 1205 Betaplate™) were soaked in 0.1% bovine serum albumin in distilled/deionized water for 1 hour at room temperature. Binding of radiolabeled $^{125}$I-salmon calcitonin (sCT; specific activity about 2000 Ci/mmol; stock diluted to 1 nM prior to use) was performed in a Beckman 96 deep-well Polypropylene titer plate in a volume of 500 µl. Additions are made in the following order:

Total binding
275 µl assay buffer (50 mM tris-HCl, pH 7.5; 10 mM $MgCl_2$;
1 mM EGTA; 0.2% bovine serum albumin; 0.2 nM PMSF;
1 mg/ml bacitracin)
25 µl test compound (or 5 µl of extracts plus 20 µl of assay buffer)
100 µl renal plasma membrane (1:2 dilution from stock)
Vortex (adapter needed for 96 well format), then add
100 µl labeled sCT (1:4 dilution from 1 nM stock)
Nonspecific binding
275 µl assay buffer
25 µl unlabeled sCT
100 µl renal plasma membrane (1:2 dilution from stock)
Vortex, then add
100 µl labeled sCT (1:4 dilution from 1 nM stock)

Samples were incubated for 1 hour at room temperature. Samples were harvested with a cell harvester designed for 96 deep-well titer plate. The filtermats were washed with 3 cycles, 4 seconds of ice-cold 0.9% saline. The filtermats were dried in 90° C. oven for 20 min., and were then bagged, 19 ml of Beta-Scint (LKB) scintillation fluid added, and sealed. The filters were counted for a period of 2 minutes per sample utilizing an LKB Betaplate Reader.

The results obtained in this standard pharmacological test procedure showed that {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one competitively inhibited the binding of calcitonin to the calcitonin receptor with an $IC_{50}$ of 0.010 mg/ml).

The second in vitro standard pharmacological test procedure determines the ability of the compound to be evaluated to act as a calcitonin agonist, by measuring the levels of cAMP produced in response to the test compound. The following briefly describes the procedure used and the results obtained.

cAMP was generated in T-47D cells (a human mammary carcinoma cell line available from the American Type Culture Collection, Rockville, Md., USA) according to the following procedure. T-47D cells were seeded at $5 \times 10^4$ cells per well in a 96 well plate and incubated overnight in growth media (RPMI-1640 medium and 10% fetal calf serum) at 37° C. in a cell incubator. After the incubation was completed, the growth medium was aspirated from the cells in the plate. The cells were washed once with 200 µl of prewarmed sample buffer (RPMI-1640 medium; 10% fetal calf serum; 20 mM HEPES buffer, pH 7.2, and 10 µM 3-isobutyl-1-methylxanthine (IBMX). Sample buffer (100 µl) containing the compound to be evaluated was added to each well and the plate was incubated in a 37° C. water bath for 10 min. The medium was aspirated from each well and 200 µl 0.01N HCl were added to the cells. After shaking the plate for 10 min, the supernatants were removed and stored at −80° C.

cAMP levels were measured using a scintillation proximity assay (SPA) system (Amersham) according to the manufacturer's protocol. cAMP standards (range: 0.2 to 12.8 pmoV 100 ul) and samples were diluted in 50 mM acetate buffer, pH=5.8 (assay buffer). Fifty ul of each standard and sample were pipetted into individual wells, followed by 50 ul of $^{125}$I-cAMP. Fifty ul of antiserum was added to all wells with the exception of the non-specific binding wells (NSB). Fifty ul of the SPA anti-rabbit reagent was added to all wells. The assay plate was sealed and mixed on an orbital shaker for 15–20 hours at room temperature The amount of $^{125}$I-cAMP bound to fluormicrospheres was determined by counting the plate in a LKB betaplate counter for 2 minutes.

Intracellular cAMP levels in the T-47D cells following salmon calcitonin stimulation for 10 rain at 37° C. are as follow:

| Calcitonin (nM) | cAMP (pmol/ml) |
| --- | --- |
| 0 (Basal) | 1 |
| 0.0001 | 2 |
| 0.001 | 13 |
| 0.01 | 105 |
| 0.1 | >640 |

When evaluated in this standard pharmacological test procedure, {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclootadecen-3 (5H)-one had an $EC_{50}$ of 0.3 µg/ml, demonstrating that this compound was a potent calcitonin agonist, and is useful in inhibiting bone resorption.

The ability of {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one to inhibit bone resorption also demonstrated in a third in vitro standard pharmacological test procedure. Briefly, osteoclasts were isolated from neonatal rat long bones by mincing the bones in Medium 199 containing Hank's salts (3 ml per 10 bones from each of 5 animals). Osteoclasts were dislodged from the bone fragments by aspirating the bone fragments 50 times into and out of a transfer pipette. 100 µl of the resulting cell suspension from each animal was then plated onto each of 3 (per dose) 4.4 $mm^2$ slices of devitalized bovine femoral cortical bone that had been placed in the wells of a 96 well plate and pre-wetted with 100 µl of the medium. The osteoclasts were then allowed to adhere for 25 minutes at 37° C. The slices, with adherent osteoclasts, were then rinsed in 5 ml of medium to remove non-adherent cells. The slices were then transferred to Medium 199 containing Earle's salts with only 0.7 g/L $NaHCO_3$ (to ensure that the medium equilibrates to a pH of 6.8–7.1 in a 5% $CO_2$ atmosphere) and 10% heat-inactivated fetal bovine serum. After a 24 h incubation at 37° C. in a humidified 5% $CO_2$/95% air atmosphere, the slices were removed from the culture medium and the cells stripped from the bone surface using sonication for two 15 second bursts in 0.25M $NH_4OH$. The excavations (pits) made by the osteoclasts in the surface of the bone were visualized by staining with 1% toluidine blue for 3 minutes and bone resorption quantified microscopically by counting the number of pits excavated per slice. An $IC_{50}$ value of 0.8 pg/ml was obtained, demonstrating that {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one has the ability to inhibit bone resorption.

{5R*-[6R*, 7S*, 8R*, 9R*, 12S*, 16S*, 18S*, 19S*, (13E)]} 4, 7, 19-Trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one was also evaluated in an in vivo standard pharmacological test procedure that measures the effect of the test compound on serum calcium levels. Agents that inhibit bone resorption, such as calcitonin, regulate circulating calcium levels by inhibiting osteoclast mediated osteolysis and thereby inhibit the release of calcium from bone. The decrease in serum calcium levels following drug treatment indicates bone sparing activity. Calcitonin acts on specific membrane receptors of the bone resorbing osteoclast cells eliciting second messenger events such as increased cAMP generation that leads to inhibition of the cell's motility and inhibition of its bone resorbing functional activity. If bone turnover activity is high, such as in the young growing rat, this rapid inhibition in bone resorption is reflected by a transient decrease in circulating calcium. The following briefly describes the procedure used and results obtained in the in vivo standard pharmacological test procedure in young growing rats. Young adult male rats weighing 160–170 g were held for at least 72 hours after receipt to acclimatize to colony conditions and then were randomly assigned to groups of 5–7 rats/group for treatment. The rats were administered vehicle or test compound, and at intervals between 0.5 and 3 hours after dosing, 1.0 ml of blood was collected from each rat under ketamin/acepromazine anesthesia via tail artery or (terminal via) cardiac puncture. Serum was evaluated for total calcium using a NOVA 7+7 blood analyzer.

The following table summarizes the results for {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one (referred to as the compound of Formula I) and calcitonin. In this standard pharmacological test procedure, all animals were dosed at 0 hours. For animals treated with the compound of Formula I, animals were bled sequentially. For animals treated with salmon calcitonin and untreated normal animals, a different group was used at each time point.

| Treatment[a] | 0.5 hours[b] | | 1.5 hours[b] | | 3.0 hours[b] | |
|---|---|---|---|---|---|---|
| | N | Serum Calcium[c] | N | Serum Calcium[c] | N | Serum Calcium[c] |
| Cmpd Formula I 10 mg/kg, i.p. | 8 | 10.73 ±0.13 | 8 | 10.21** ±0.17 | 7 | 9.99** ±0.09 |
| Cmpd Formula I 30 mg/kg, i.p. | 8 | 10.60 ±0.05 | 8 | 10.43* ±0.12 | 6 | 10.18 ±0.05 |
| Cmpd Formula I 100 mg/kg, i.p. | 8 | 10.29** ±0.13 | 8 | 10.19** ±0.09 | 8 | 10.06* ±0.10 |
| Salmon Calcitonin 5 IU/rat, s.c. | 6 | 8.17** ±0.09 | 6 | 7.45** ±0.07 | 6 | 6.65** ±0.09 |
| Normals | 6 | 10.92 ±0.13 | 6 | 10.88 ±0.10 | 6 | 10.40 ±0.11 |

[a]All animals were dosed at 0 hours. For animals treated with the compound of Formula I, animals were bled sequentially. For animals treated with salmon calcitonin and untreated normal animals, a different group was used at each time point.
[b]Time after dosing
[c]Mean ± SEM
*$p < 0.05$ vs corresponding normals
**$p < 0.01$ vs corresponding normals The results of the in vitro and in vivo standard pharmacological test procedures showed that {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one bound to the calcitonin receptor, acted as a potent agonist at the calcitonin receptor, and significantly reduced serum calcium levels demonstrating its ability to inhibit bone resorption. Based on these results, {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one is useful in treating or inhibiting osteoporosis, bone loss secondary to glucocorticoid and other drug treatments, and other metabolic bone diseases such as Paget's disease and hypercalcemia resulting from malignancy.

{5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one can be formulated neat or with a pharmaceutical carrier. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

{5R*-[6R*, 7S*, 8R*, 9R*, 12S*, 16S*, 18S*, 19S*, (13E)]} 4, 7, 19-Trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one may be administered rectally in the form of a conventional suppository. For administration by intranasal or intrabronchial inhalation or insufflation, {5R*-[6R*, 7S*, 8R*, 9R*, 12S*, 16S*, 18S*, 19S*, (13E)]} 4, 7, 19-Trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one may be formulated into an aqueous or partially aqueous solution, which can then be utilized in the form of an aerosol. {5R*-[6R*, 7S*, 8R*, 9R*, 12S*, 16S*, 18S*, 19S*, (13E)]} 4, 7, 19-Trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane coveting a reservoir containing the active ingredient with or without a carrier, or a matrix containing the active ingredient. Other occlusive devices are known in the literature.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The dosage requirements vary with the particular compositions employed, the route of administration, the severity of the symptoms presented and the particular subject being treated. Based on the results obtained in the standard pharmacological test procedures, projected daily intravenous dosages of {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one, would be 0.1–10 mg/kg. Projected daily oral dosages of {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one would be 1–25 mg/kg.

Treatment will generally be initiated with small dosages less than the optimum dose of the compound. Thereafter the dosage is increased until the optimum effect under the circumstances is reached; precise dosages for oral, parenteral, intranasal, intrabronchial, transdermal, or rectal administration will be determined by the administering physician based on experience with the individual subject treated. In general, {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one is most desirably administered at a concentration that will generally afford effective results without causing any harmful or deleterious side effects.

EXAMPLE 1

Isolation and Fermentation of NRRL 21370

Streptomyces spp. NRRL 21370, was isolated from a soil sample collected from the side of a highway in North Miami, Fla., and samples thereof have been deposited with the ARS Patent Culture Collection at the USDA/ARS Northern Regional Research Center. The original soil sample was air dried at room temperature and then heat treated at 120° C. for 1 hour. The soil sample was applied to Actinomycetes Isolation Agar containing 50 pg/ml nystatin, 50 μg/ml cyclohexamide, and 10 μg/ml rifampicin. The strain was identified to be a member of the genus Streptomyces and produces spore chains which are large with spacers and of the type Spirales.

Strain NRRL 21370 was grown and maintained on Starch Casein Agar which contains:

| | |
|---|---|
| Hayashi Soluble Starch (Hayashi Pure Chemical Industries Ltd. Japan) | 10 g/liter |
| Casein (Sigma) | 1 g/liter |
| Potassium Phosphate, Dibasic (Mallinckrodt) | 0.5 g/liter |
| $MgSO_4.7H_2O$ (Sigma) | 0.5 g/liter |
| Yeast Extract (Difco) | 1 g/liter |

Grown on this medium the spore mass is gray while the reverse of the mycelium is tan to maroon with a brown diffusible pigment.

The best utilized carbon sources were glucose, rhamnose, fructose, raffinose, mannitol, and sucrose; and the less well utilized carbon sources were xylose and inositol. Carbon sources arabinose and cellulose were not utilized. The microorganism is NaCl tolerant up to and including 10%.

NRRL 21370 was grown on Starch Casein Agar demonstrated good growth after 14 days at 28° C. The plates were then scraped and the mycelia and spore mass were placed in a tube containing glass beads plus a storage solution of 5% lactose and 10% glycerol. The tubes were then vortexed until a turbid solution was obtained. Fifteen milliliters of the turbid solution was pipetted into 2-two liter flasks containing 400 mls of the seed media which contained:

| | |
|---|---|
| Glucose | 20 g/liter |
| Pharmamedia (Trader's Protein) | 25 g/liter |
| $(NH_4)_2SO_4$ | 3 g/liter |
| $ZnSO_4.7H_2O$ | 0.03 g/liter |
| $CaCO_3$ | 4 g/liter |
| Yeast Extract (Difco) | 5 g/liter |

These flasks were shaken at 250 RPM at 28° C. for 48 hours. The seed material was then transferred to New Brunswick Scientific Micros 30 fermenters. The fermenter parameters included 20 liters of fermentation media, 28° C., 500 RPM, 10 liters air per minute, 5 psi above atmospheric, and 2 ml/L Polypropylene glycol 2000 as an antifoaming agent. Fermentation was conducted for 6 days followed by harvesting of the entire fermentation to provide NRRL 21370. The fermentation medium contained:

| | |
|---|---|
| Alpha Lactose | 10 g/liter |
| Soluble Starch | 30 g/liter |
| Fishmeal (Sigma) | 10 g/liter |
| $CaSO_4.2H_2O$ | 6 g/liter |
| $CaCO_3$ | 5 g/liter |

EXAMPLE 2

{5R*-[6R*, 7S*, 8R*, 9R*, 12S*, 16S*, 18S*, 19S*, (13E)]} 4, 7, 19-Trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one Procedure A The fermentation mixture was filtered through cheese cloth by suction filtration. The filtrate was extracted three times with 0.25 v/v ethyl acetate. The combined extracts were evaporated under reduced pressure to dryness. The mycelium was briefly homogenized and then extracted three times with 0.4 v/v of ethyl acetate. The ethyl acetate layers were combined and the solvent removed by rotary evaporation. The oily residues resulting from the extraction of both the filtrate and mycelium were combined and dried on a vacuum pump overnight.

The crude extract was subjected to countercurrent partition chromatography (CPC) fractionation on a high speed countercurrent chromatograph containing a "Tripple" coil column (PC, Inc.). A 1:3:3:3 v/v/v/v of n-hexane, ethyl acetate, methanol and water was mixed and allowed to settle overnight. The lower layer was pumped into the CPC column as the stationary phase. The upper layer was used as the mobile phase. After 2 hours, the lower and upper layer were switched. The CPC run was completed after 4 hours. The fractions were tested in the in vitro calcitonin receptor binding standard pharmacological procedure (described above) and the crude desired product was found to elute from the CPC between 30 and 33 minutes. The active fractions were pooled and evaporated under reduced pressure to dryness.

The pooled CPC fractions were dissolved in 1 volume of 10% aqueous methanol and extracted three times with 1 volume of n-hexane. The desired product remained present in the aqueous methanol layer. The aqueous methanol layers were combined and evaporated under reduced pressure to dryness.

The aqueous methanol portion obtained above was subjected to two subsequent HPLC fractionation's (Waters HPLC with Millennium software) using the following conditions:

a) 81.5 mg of material dissolved in 5 ml of 1 v/v acetonitrile/water was injected into a preparative C18-column (40×100 mm, Deltapak, 15 micron) with a flow rate of 20 ml/minute for each separation run and monitored by photodiode array (PDA) at 314 nm. Separation conditions were isocratic using 2 volumes of water to 3 volumes of acetontrile over 100 minutes. The desired material eluted between 75 and 90 minutes. The desired fractions were combined and evaporated to under reduced pressure to dryness.

b) 18.3 mg of crude material from the preparative column above dissolved in 0.08 ml of DMSO was injected into two semipreparative C18-columns in series (25×100 mm, Nova Pak, 10 micron) with a flow rate of 10 ml/minute for each separation run and monitored by PDA at 270 nm. Separation conditions were isocratic using 1 volume of water to 4 volumes of acetonitrile over 27 minutes. The desired fraction eluted between 22 and 25 minutes. The desired fractions were combined and evaporated under reduced pressure dryness.

The material obtained from semipreparative chromatography was partitioned between 1 volume of chloroform and 1 volume of 50% aqueous methanol. The desired product remained with the chloroform layer. The chloroform layer was evaporated and purified product was precipitated with acetonitrile m.p.: greater than 195° C. (dec). The optical rotation of the purified compound was determined to be alphaD: −97.4 (c=0.195,acetone).

The following represent modifications of Procedure A, with procedure B being preferred for scale up.

Procedure B

The initial crude ethyl acetate extract was obtained as in Procedure A. This material was partitioned between 1 volume of n-hexane and 1 volume of 10% aqueous methanol. The desired product remained with the aqueous methanol layer. This material was subjected to CPC fractionation under the same conditions as described in Procedure A, and the desired fractions were combined and evaporated under reduced pressure.

This oily residue was then subjected to column chromatography on Sephadex LH20 (130 g dry weight) in ethanol (315 ml). The product, identified by a characteristic yellow color, was eluted with ethanol. The methanol eluate was reduced to a small volume and the desired product was precipitated with ethanol. An analytical sample was prepared by crystallization from ethanol.

Procedure C

The initial crude ethyl acetate extract was obtained as described in Procedure A. This material was partitioned between 1 volume n-hexane and 1 volume of 10% aqueous methanol, and followed by subsequent CPC fractionation under the same conditions as described in Procedure A. This produced an oily residue as described in Procedure B.

The resulting material was precipitated with acetonitrile. An analytical sample was prepared by crystallization from ethanol.

The following tables show the proton and carbon magnetic resonances for {5R*-[6R*, 7S*, 8R*, 9R*, 12S*, 16S*, 18S*, 19S*, (13E)]} 4, 7, 19-trihydroxy-2, 6, 8, 12, 12, 14, 16, 18-heptamethyl-6, 7, 8, 9, 10, 11, 12, 15, 16, 17, 18, 19-dodecahydro-1, 19:5, 9-diepoxybenzocyclooctadecen-3 (5H)-one. The resonance assignments are based on the numbering system in the figure below.

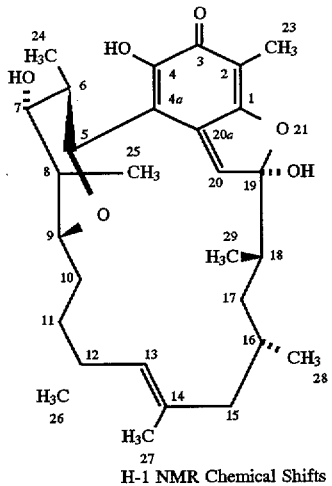

H-1 NMR Chemical Shifts

| Proton* | δ# | Multiplicity% | δ$ | Multiplicity% |
|---|---|---|---|---|
| C-4OH | 8.078 | s | 8.145 | s |
| H-5 | 4.335 | d, J=10.5 | 4.512 | d, J=10.5 |
| H-6 | 1.680 | tq, J=10.5,6.6 | 2.2 | obscured |
| H-7 | 3.541 | dt, J=10.5, 4.8 | 3.610 | dt, J=10.3, 4.4 |
| C-7 OH | 3.920 | d, J=4.8 | 3.820 | d, J=4.4 |
| H-8 | 1.857 | qdd, J=6.8, 4.8, 2.6 | 2.2 | obscured |
| H-9 | 3.505 | ddd, J=10.8, 2.6, 1.1 | 3.434 | ddd, J=10.9, 2.0, 1.0 |
| H-10a | 1.55 | m | 1.5 | obscured |
| H-10b | 1.2 | m | 1.11 | tdd, J=12.8, 5.3, 1.0 |
| H-11a | 1.3 | m | 1.39 | tdd, J=12.8, 11.4, 2.6 |
| H-11b | 1.3 | m | 1.27 | tdd, J=12.8, 5.3, 2.4 |
| H-12 | 2.322 | tq, J=9.9, 6.6 | 2.324 | ddqd, J=11.4, 9.8, 6.5, 2.4 |
| H-13 | 4.614 | d, J=9.9 | 4.687 | d, J=9.8 |
| H-15a | 2.101 | dm, J=17.2, unresolved | 2.068 | bd, J=17.1 |
| H-15b | 1.666 | dd, J=17.2, 2.0 | 1.5 | obscured |
| H-16 | 1.950 | dqdt, J=11.1, 6.5, 4.0, 2.0 | 2.2 | obscured |
| H-17a | 1.65 | m | 1.703 | td, J=12.8, 2.0 |
| H-17b | 1.424 | ddd, J=12.9, 11.1, 3.2 | 1.5 | obscured |
| H-18 | 2.390 | dqd, J=12.9, 6.7, 3.2 | 2.537 | dqd, J=12.8, 6.7, 3.2 |
| C-19-OH | 6.499 | s | 6.610 | s |
| H-20 | 7.165 | s | 7.350 | s |
| $CH_3$-23 | 1.817 | s | 1.985 | s |
| $CH_3$-24 | 0.866 | d, J=6.6 | 1.058 | d, J=6.6 |
| $CH_3$-25 | 0.923 | d, J=6.8 | 0.962 | d, J=6.5 |
| $CH_3$-26 | 0.845 | d, J=6.6 | 0.933 | d, J=6.5 |
| $CH_3$-27 | 1.585 | bs | 1.577 | bs |
| $CH_3$-28 | 0.917 | d, J=6.5 | 1.034 | d, J=6.9 |
| $CH_3$-29 | 0.688 | d, J=6.7 | 0.752 | d, J=6.7 |

*See Figure for numbering system used
Solution in Acetone-d6; Chemical shifts are reported relative to TMS and were measured relative to internal Acetone-d5 = 2.02 ppm
%s = singlet, d = doublet, t = triplet, q = quartet, b = broad, m = multiplet; Coupling constants, J, are in Hz and are the average of all multiplets in which they are measured.
$Solution in Benzene-d6: Acetone-d6 1:1; Chemical shifts are reported relative to TMS and were measured relative to internal Benzene-d5 = 7.27 ppm -continued

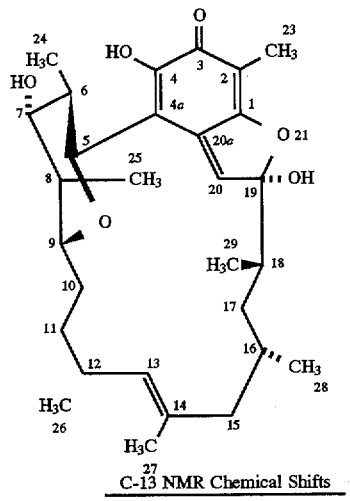

C-13 NMR Chemical Shifts

| Carbon No.* | Chemical Shift# | Chemical Shift$ | APT results% |
|---|---|---|---|
| C-1 | 168.60 | 168.67 | np-$sp^2$-C |
| C-2 | 119.14 | 119.25 | np-$sp^2$-C |
| C-3 | 182.13 | 182.26 | np-$sp^2$-C |
| C-4 | 146.85 | 146.83 | np-$sp^2$-C |
| C-4a | 130.22 | 130.30 | np-$sp^2$-C |
| C-5 | 77.73 | 77.82 | CH |
| C-6 | 38.17 | 38.28 | CH |
| C-7 | 78.72 | 78.67 | CH |
| C-8 | 40.85 | 40.83 | CH |
| C-9 | 76.32 | 76.44 | CH |
| C-10 | 33.46 | 33.42 | $CH_2$ |
| C-11 | 35.87 | 35.79 | $CH_2$ |
| C-12 | 33.62 | 33.65 | CH |
| C-13 | 129.88 | 129.88 | $sp^2$-CH |
| C-14 | 132.12 | 132.01 | np-$sp^2$-C |
| C-15 | 46.09 | 46.02 | $CH_2$ |
| C-16 | 26.50 | 26.45 | CH |
| C-17 | 39.75 | 39.67 | $CH_2$ |
| C-18 | 41.47 | 41.46 | CH |
| C-19 | 104.26 | 104.35 | np-$sp^3$-C |
| C-20 | 141.33 | 141.60 | $sp^2$-CH |
| C-20a | 110.99 | 110.94 | np-$sp^2$-C |
| C-23 | 7.62 | 7.93 | $CH_3$ |
| C-24 | 13.29 | 13.49 | $CH_3$ |
| C-25 | 19.92 | 19.87 | $CH_3$ |
| C-26 | 22.70 | 22.90 | $CH_3$ |
| C-27 | 19.72 | 20.01 | $CH_3$ |
| C-28 | 7.18 | 7.32 | $CH_3$ |
| C-29 | 12.66 | 12.84 | $CH_3$ |

*See Figure for numbering system used
Solution in Acetone-d6; Chemical shifts are reported relative to TMS and were measured relative to internal Acetone-d6 methyl carbon = 29.8 ppm
%APT = attached proton test; np = nonprotonated
$Solution in Benzene-d6: Acetone-d6 1:1; Chemical shifts are reported relative to TMS and were measured relative to internal Acetone-d6 methyl carbon = 29.8 ppm Mass spectra were run on a Finnigan MAT 8230 and were obtained in the ei(electron impact) mode at 70 eV. HRMS (high resolution mass spectra) were performed using PKF (perfluorokerosene) as an internal standard. MS m/z (rel intensity) 486($M^+$, 100), 468(M-28, 86), 220(M-266, 96), 193(M-293, 80); HRMS m/z 486.297879($M^+$ calcd for $C_{29}H_{42}O_6$ 486.297879).

What is claimed is:

1. A method of inhibiting bone resorption in a mammal which comprises administering to said mammal an effective amount of a compound of Formula I having the structure
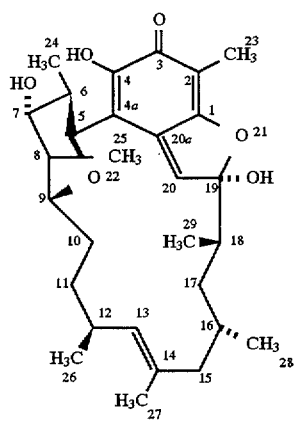
said mammal.
2. A method of treating or inhibiting osteoporosis in a mammal which comprises administering to said mammal an effective amount of a compound of Formula I having the structure
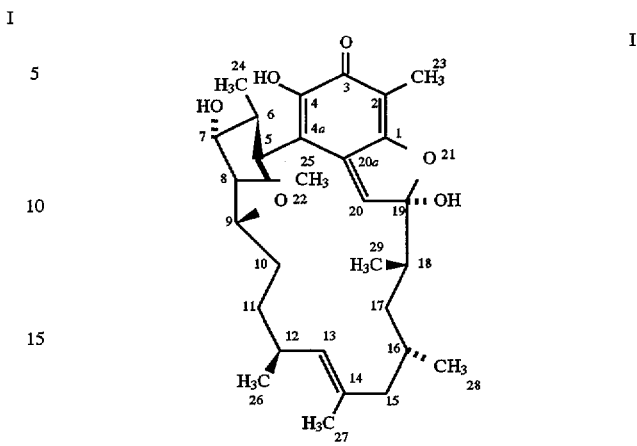
to said mammal.
* * * * *